United States Patent [19]

Spivack et al.

[11] Patent Number: 4,560,799
[45] Date of Patent: Dec. 24, 1985

[54] TRI- AND TETRA-(SUBSTITUTED HYDROXYPHENYLTHIO) ALKANE AND CYCLOALKANE STABILIZERS AND STABILIZED COMPOSITIONS

[75] Inventors: John D. Spivack; Stephen D. Pastor, both of Spring Valley, N.Y.

[73] Assignee: Ciba-Geigy Corporation, Ardsley, N.Y.

[21] Appl. No.: 576,978

[22] Filed: Feb. 3, 1984

[51] Int. Cl.[4] ............................................. C07D 149/00
[52] U.S. Cl. ........................................ 568/47; 524/331
[58] Field of Search ............................ 568/47; 524/331

[56] References Cited

U.S. PATENT DOCUMENTS

| | | | |
|---|---|---|---|
| 3,310,587 | 3/1967 | O'Shea | 568/47 |
| 3,474,147 | 10/1969 | Lehikoinen | 568/47 |
| 3,576,883 | 4/1971 | Neuworth | 568/47 |
| 3,704,326 | 11/1972 | Song | 568/47 |
| 3,704,327 | 11/1972 | Neuworth | 568/47 |
| 3,786,100 | 1/1974 | Neuworth | 568/47 |
| 3,897,500 | 7/1975 | Neuworth | 568/47 |
| 3,956,359 | 5/1976 | Neuworth | 568/47 |
| 4,108,831 | 8/1978 | Cottman | 568/47 |
| 4,330,462 | 5/1982 | Keck et al. | 568/47 |

FOREIGN PATENT DOCUMENTS

| | | |
|---|---|---|
| 54-163536 | 12/1979 | Japan. |
| 55-9041 | 1/1980 | Japan. |
| 55-17316 | 2/1980 | Japan. |

OTHER PUBLICATIONS

M. B. Neuworth et al., J. Medicinal Chem., 13, 722 (1970).

*Primary Examiner*—Donald G. Daus
*Assistant Examiner*—Cecilia Shen
*Attorney, Agent, or Firm*—Luther A. R. Hall

[57] ABSTRACT

Organic materials are stabilized against thermal, oxidative and photo-degradation by incorporating therein an effective amount of a compound of formula I

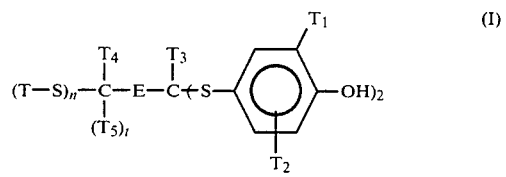

wherein $T_1$ $T_2$ independently are alkyl, cycloalkyl, phenyl, aralkyl, $T_2$ may also be hydrogen, T is alkyl, phenyl or substituted hydroxyphenyl, E is a direct bond, alkylene, cycloalkylene, phenylene or $-CH_2CH(ST)CH_2-$, $T_3$ and $T_4$ are independently hydrogen, alkyl or cycloalkyl; or together are alkylene, $T_5$ is hydrogen, alkyl or phenyl, n is 1 or 2, t is 0 or 1, and t is 2-n. Polyolefins, ABS resins, natural and synthetic rubbers and polyesters are particularly well stabilized by the compounds of formula I.

14 Claims, No Drawings

TRI- AND TETRA-(SUBSTITUTED HYDROXYPHENYLTHIO) ALKANE AND CYCLOALKANE STABILIZERS AND STABILIZED COMPOSITIONS

The present invention pertains to alkane or cycloalkane moieties containing three or four substituted hydroxyphenylthio groups which are useful as stabilizers for organic materials and to stabilized compositions containing said compounds.

BACKGROUND OF THE INVENTION

Organic polymeric materials such as plastics, rubber and resins, and synthetic, lubricating and mineral oils are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered. These and other undesirable degradative effects may originate as a result of thermal degradation, oxidation, photodegradation or some combination of these processes with the organic materials under conditions which are not well understood.

It has now been determined that the compounds of this invention possess an unusual combination of desirable properties which makes them particularly effective and useful as stabilizers. The compounds are particularly effective in protecting polyolefins, high impact polystyrene, rubbers such as polybutadiene and styrene-butadiene rubber, and other elastomers wherein retention of elasticity and inhibition of crosslinking, crazing, discoloration, odor formation and exudation are basic requirements.

The hydroxyphenylthio compounds found useful in stabilizing organic substrates are new materials.

A related series of U.S. Pat. Nos. 3,576,883; 3,786,100; 3,897,500 and 3,956,359 disclose keto substituted alkylidenedithiobisphenols wherein bis(3,5-di-tert-butyl-4-hydrophenyl) groups and various alkylidene bridging groups are present. In all cases a methyl substituent must appear on the alkylidene linking member of these compounds. The compounds of these patents are found useful for reducing blood cholesterol levels in warm-blooded animals and no mention or suggestion of their possible use as stabilizers is made.

M. B. Neuworth et al., J. Medicinal Chemistry, 13, 722 (1970) describes the same compounds as disclosed in the four patents mentioned supra as well as a number of comparable alkylidenedithiophenols having a variety of substituent groups on the phenyl ring and on the linking alkylidene member. Again, the only utility given for said compounds is for hypocholesterolemic activity in warm-blooded animals.

The instant compounds are structurally clearly different from the bis(substituted hydroxyphenylthio) compounds of this publication.

Three Japanese Kokai 79/163,536; 80/9,041 and 80/17,316 (CA, 93, 71280x (1980); CA, 93, 94980q (1980) and CA, 93, 149970u (1980) respectively) describe 2,2-bis(3,5-di-tert-butyl-4-hydroxyphenylthio)-propane as a hypocholesterolemic agent.

U.S. Pat. No. 3,704,327 discloses bis(3-methyl-5-tert-butyl-4 hydroxyphenylthio)methane and 1,1-bis(3-methyl-5-tert-butyl-4-hydroxyphenylthio)ethane as antioxidants for rubber. The instant compounds differ structurally from these prior art compounds by containing three or four substituted hydroxyphenylthio moieties on the alkane or cycloalkane group.

OBJECTS OF THE INVENTION

It is the primary object of this invention to provide a class of hydroxyphenylthio compounds which exhibit a broad range of improved stabilization performance characteristics and to provide for stabilized compositions containing said compounds.

DETAILED DISCLOSURE

The instant invention pertains to organic materials stabilized against the deleterious effects of thermal, oxidative and photo-degradation by the incorporation therein of an effective amount of a compound of formula I

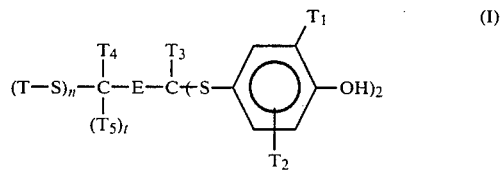

wherein $T_1$ and $T_2$ are independently alkyl of 1 to 12 carbon atoms, cycloalkyl of 5 to 6 carbon atoms, phenyl, phenyl substituted by alkyl of 1 to 12 carbon atoms, aralkyl of 7 to 9 carbon atoms or said aralkyl substituted by alkyl of 1 to 12 carbon atoms, $T_2$ may also be hydrogen, T is alkyl of 1 to 24 carbon atoms, phenyl, phenyl substituted by alkyl of 1 to 12 carbon atoms, or the group

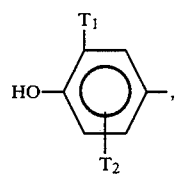

E is a direct bond, alkylene of 1 to 11 carbon atoms, cycloalkylene of 5 to 6 carbon atoms or phenylene, or is the group

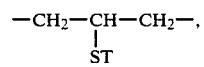

$T_3$ and $T_4$ are independently hydrogen, alkyl of 1 to 30 carbon atoms, said alkyl substituted by phenyl or by phenyl substituted by alkyl of 1 to 12 carbon atoms, cycloalkyl of 5 to 6 carbon atoms, or $T_3$ and $T_4$ together are straight- or branched-chain alkylene of 3 to 7 carbon atoms when E is methylene, $T_5$ is hydrogen, alkyl of 1 to 4 carbon atoms or phenyl, n is 1 or 2, t is 0 or 1 and t is 2-n.

The preferred compounds of the instant invention are those wherein $T_2$ is in the ortho position relevant to the hydroxy group.

When any of T to $T_5$ and/or E represent alkyl, cycloalkyl, aralkyl, cycloalkenyl, alkylene, cycloalkylene and/or phenylene, examples of such groups are as follow:

alkyl of 1 to 30 carbon atoms is, for example, methyl, ethyl, isopropyl, n-butyl, sec-butyl, tert-butyl, isoamyl, tert-amyl, n-hexyl, 2-ethylhexyl, n-octyl, tert-octyl, n-dodecyl, tert-dodecyl, n-octadecyl, eicosyl or triacontyl;

cycloalkyl of 5 to 6 carbon atoms is cyclopentyl or cyclohexyl;

aralkyl of 7 to 9 carbon atoms is, for example, benzyl, alpha-methylbenzyl or alpha, alpha-dimethylbenzyl;

cycloalkenyl of 5 to 6 carbon atoms is, for example, cyclopent-3-enyl or cyclohex-3-enyl;

alkylene of 1 to 11 carbon atoms is, for example, methylene, ethylene, trimethylene, 2,2-dimethylpropan-1,3-diyl, tetramethylene, pentamethylene, octamethylene or undecamethylene;

cycloalkylene of 5 to 6 carbon atoms is, for example, cyclopentylene or 1,4-cyclohexylene; and phenylene is o-phenylene, m-phenylene or p-phenylene.

Preferably $T_1$ and $T_2$ are independently straight- or branched-chain alkyl of 1 to 8 carbon atoms, for example, methyl, isopropyl, n-butyl, sec-butyl, tert-butyl, tert-amyl or tert-octyl.

Especially preferred are the groups methyl, tert-butyl, tert-amyl and tert-octyl.

Most preferably $T_1$ is methyl or tert-butyl and $T_2$ is tert-butyl.

Most preferably of all, both $T_1$ and $T_2$ are ortho to the hydroxy group and both are tert-butyl.

Preferably T is alkyl of 1 to 18 carbon atoms, most preferably 7 to 18 carbon atoms, or is the group

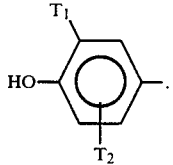

Preferably E is a direct bond, alkylene of 1 to 6 carbon atoms or the group

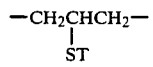

Preferably $T_3$ and $T_4$ are independently hydrogen or alkyl of 1 to 4 carbon atoms.

Preferably $T_3$ and $T_4$ together are trimethylene or 2,2-dimethylpropan-1,3-diyl when E is methylene.

Preferably $T_5$ is hydrogen or methyl.

The stabilizer compounds are prepared by reacting the appropriate 4-mercaptophenol with the appropriate bis-carbonyl compound in the presence of a strong acid catalyst, such as hydrogen chloride. The reaction is preferably conducted in an inert organic solvent, such as methanol, heptane, benzene or toluene. The reaction temperature generally ranges from 0° to 100° C. The starting materials are generally items of commerce or can be prepared by known methods.

When the instant compounds of formula I where n is 1 are prepared from alpha, beta-unsaturated carbonyl compounds, the appropriate mercaptan or 4-mercaptophenol is first added across the activated double bond using a tertiary amine as a catalyst, such as triethylamine, followed by reaction of the appropriate 4-mercaptophenol to the carbonyl group in the presence of a strong acid catalyst such as boron trifluoride-etherate.

Compounds of this invention are particularly effective in stabilizing organic materials such as plastics, polymers and resins in addition to mineral and synthetic fluids such as lubricating oils, circulating oils, etc.

Substrates in which the compounds of this invention are particularly useful are polystyrene, including impact polystyrene, ABS resin, SBR, polyisoprene, as well as natural rubber, polyesters including polyethylene terephthalate and polybutylene terephthalate, including copolymers, poly-alpha-olefins and lubricating oils such as those derived from mineral oil.

In general, polymers which can be stabilized include:

1. Polymers of monoolefins and diolefins, for example polyethylene (which optionally can be crosslinked), polypropylene, polyisobutylene, polybutene-1 polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyethylene or with polyisobutylene.

3. Copolymer of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/ethyl acrylate, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene norbornene.

4. Polystyrene.

5. Random copolymers of styrene or α-methylstyrene with dienes or acrylic derivatives, such as, for example, styrene/butadiene, styrene/acrylonitrile, styrene/alkyl methacrylates, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, polymers from halogen-containing vinyl compounds, as for example, polyvinyl chloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamides and polyacrylonitrile.

9. Copolymers from the monomers mentioned under (8) with each other or with other unsaturated monomers, such as, for instance, acrylonitrile/butadiene, acrylonitrile/alkyl acrylate or acrylonitrile/vinyl chloride copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallylmelamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer.

13. Polyphenylene oxides and sulfides.

14. Polyurethanes which are derived from polyethers, polyesters or polybutadienes with terminal hydroxyl groups on the one side and aliphatic or aromatic polyisocyanates on the other side, as well as precursors thereof.

15. Polyamides and copolyamides which are derived from diamines and dicarboxylic acid and/or from aminocarboxylic acids of the corresponding lactams, such as polyamide 4, polyamide 6, polyamide 6/6, polyamide 6/10, polyamide 11, polyamide 12, poly-2,4,4-trimethylhexamethylene terephthalamide or poly(m-phenylene isophthalamide), as well as copolymers thereof with polyethers, such as for instance, with polyethylene glycol, polypropylene glycol or polytetramethylene glycols.

16. Polyureas, polyimides and polyamide-imides.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates as well as block copolyether-esters derived from polyethers having hydroxyl end groups.

18. Polycarbonates.

19. Polysulfones and polyethersulfones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides and aromatic diepoxides.

26. Natural polymers, such as cellulose, rubber, gelatin and derivatives thereof which are chemically modified in a polymer-homologous manner, such as cellulose acetates, cellulose propionates and cellulose butyrates, or the cellulose ethers, such as methyl cellulose.

27. Naturally occurring and synthetic organic materials which are pure monomeric compounds or mixtures of such compounds, for example mineral oils, animal and vegetable fats, oils and waxes, or oils, fats and waxes based on synthetic esters (e.g. phthalates, adipates, phosphates or trimellitates) and also mixtures of synthetic esters with mineral oils in any weight ratios, which materials may be used as plasticizer for polymers or as textile spinning oils, as well as aqueous emulsions of such materials.

28. Aqueous emulsions of natural or synthetic rubber, e.g. natural latex or latices of carboxylated styrene/butadiene copolymers.

In general, the stabilizers of this invention are employed in from about 0.01 to about 5% by weight of the stabilized composition, although this will vary with the particular substrate and application. An advantageous range is from about 0.05 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:

1. Antioxidants 1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(-methylcyclohexyl)-4,6-dimethylphenol
2,6-di-octadecyl-4-methylphenol
2,4,6-tricyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)

4,4'-thio-bis-(6-tert-butyl-2-methylphenol)

1.4. Alkylidene-bisphenols, for example, 2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethylenglycol-bis-[3,3-bis-(3-tert-butyl-4-hydroxyphenyl)butyrate]
di-(3-tert-butyl-4-hydroxy-5-methylphenyl)-dicyclopentadiene
di-[2-(3-tert-butyl-2-hydroxy-5-methyl-benzyl)-6-tert.-butyl-4-methylphenyl]terephthalate.

1.5. Benzyl compounds, for example, 1,3,5-tri-(3,5-di-tert-butyl-4-hydroxybenzyl)-2,4,6-trimethylbenzene
bis-(3,5-di-tert-butyl-4-hydroxybenzyl)sulfide
3,5-di-tert-butyl-4-hydroxybenzylmercaptoacetic acid isooctyl ester
bis-(4-tert-butyl-3-hydroxy-2,6-dimethylbenzyl)dithiolterephthalate
1,3,5-tris-(3,5-di-tert.butyl-4-hydroxybenzyl)isocyanurate
1,3,5-tris-(4-tert.butyl-3-hydroxy-2,6-dimethylbenzyl)isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example, 4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.8. Ester of β-(5-tert-butyl-4-hydroxy-3-methylphenyl)propionic acid with monohydric or polyhydric alcohols, for example,

| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic diamide |

1.9. Amides of β-(3,5-di-tert-butyl-4-hydroxyphenyl)-propionic acid for example, N,N'-bis-(3,5-di-tert-butyl-4-hydroxyphenylpropionyl)-hexamethylenediamine
N,N'-bis-(3,5-di-tert-butyl-4-hydroxyphenylpropionyl)-trimethylenediamine
N,N'-bis-(3,5-di-tert-butyl-4-hydroxyphenylpropionyl)-hydrazine 2. UV absorbers and light stabilisers 2.1. 2-(2'-Hydroxyphenyl)-benztriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octyloxy, 3',5'-di-tert-amyl-, 3',5'-bis-(α,α-dimethylbenzyl)-derivative.

2.2. 2-Hydroxy-benzophenones, for example, the 4-hydroxy-, 4-methoxy-, 4-octyloxy, 4-decyloxy-, 4-dodecyloxy-, 4-benzyloxy, 4,2',4'-trihydroxy- and 2'-hydroxy-4,4'-dimethoxy derivative.

2.3. Ester of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butyl-phenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)sebacate, bis-(1,2,2,6,6-pentamethylpiperidiyl)sebacate, n-butyl-3,5-di-tert-butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamthylenediamine and 4-tert.octylamino-2,6-dichloro-1,3,5-s-triazine, tris-(2,2,6,6-tetramethylpiperidyl)nitrilotriacetate, tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone).

2.7. Oxalic acid diamides, for example, 4,4'-dioctyloxyoxanilide, 2,2'-di-octyloxy-5,5'-di-tert-butyloxanilide, 2,2'-di-dodecyloxy-5,5'-di-tert-butyl-oxanilide, 2-ethoxy-2'-ethyl-oxanilide, N,N'-bis-(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicycloylhydrazine, N,N'-bis-(3,5-di-tert-butyl-4-hydroxyphenylpropionyl)-hydrazine, 3-slicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearylpentaerythrityl diphosphite, tris-(2,4-di-tert-butylphenyl)-phosphite, diisodecylpentaerythrityl diphosphite, di-(2,4-di-tert-butylphenyl)pentaerythrityl diphosphite, tristearyl-sorbityl triphosphite, tetrakis-(2,4-di-tert-butylphenyl)-4,4'-diphenylylendiphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythrityl-tetrakis (β-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for eample, 4-tert-butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticizers, lubricants, emulsifiers, pigments, optical brighteners, flame-proofing agents, antistatic agents, blowing agents and thiosynergists such as dilauryl thiodipropionate or distearyl thiodipropionate.

The instant compounds of formula I are novel materials and comprise part of the instant invention.

The following examples further illustrate the embodiments of this invention. In these examples, all parts given are by weight unless otherwise specified.

EXAMPLE 1

1,1,2,2-Tetrakis(3,5-di-tert-butyl-4-hydroxyphenylthio)ethane

A solution of 23.84 grams of 2,6-di-tert-butyl-4-mercaptophenol and 3.63 grams of 40% aqueous glyoxal in 150 ml of methyl alcohol is charged into a flask under a nitrogen atmosphere and is then treated with anhydrous hydrogen chloride, with the temperature allowed to rise to 60° C. The reaction product is filtered off and recrystallized from acetonitrile:toluene to give 21.65 grams (89% yield) of white crystals, mp 221°–223° C.

Anal. Calcd. for $C_{58}H_{86}O_4S_4$: C, 71.4; H, 8.9. Found: C, 71.5; H, 9.0.

EXAMPLE 2

1,1,5,5-Tetrakis(3,5-di-tert-butyl-4-hydroxyphenylthio)-pentane

A solution of 23.84 grams of 2,6-di-tert-butyl-4-mercaptophenol and 5.01 grams of 50% aqueous glutaraldehyde in 150 ml of methyl alcohol is charged into a flask under a nitrogen atmosphere and is treated with anhydrous hydrogen chloride, with the temperature allowed to rise to 60° C. The reaction is stirred overnight, filtered and solid obtained is recrystallized twice from acetonitrile an heptane, respectively, to yield 16.73 grams (66% yield) of white crystals, mp 148°–153° C.

Anal. Calcd. for $C_{61}H_{92}O_4S_4$: C, 72.0; H, 9.1. Found: C, 72.1; H, 8.9.

EXAMPLE 3

1,1,3-Tris-(3,5-di-tert-butyl-4-hydroxyphenylthio)butane (a) 3-(3,5-Di-tert-butyl-4-hydroxyphenylthio)-n-butanal 3.12 Grams of crotonaldehyde(0.042 mole) are added dropwise over a 15 minute period at 17°–22° C. to a solution of 10.8 grams of 2,6-di-tert-butyl-4-mercaptophenol (0.044 moles) and 0.5 gram of triethylamine in 20 ml of toluene and allowed to react in a nitrogen atmosphere at room temperature for 30 minutes and then at 50°–55° C. for two hours. Analysis indicates that the reaction is substantially complete at this point. The product, isolated as a light yellow liquid, is obtained in nearly quantitative yield after stripping off volatiles at 40° to 50° C. at 0.15 mm. Hg.

(b) The product prepared in (a) (14 grams, 0.042 moles) and 20.4 grams of 2,6-di-tert-butyl-4-mercaptophenol (0.084 moles) are dissolved together in 85 ml of toluene to which is added with stirring 0.30 grams of $BF_3$-etherate. The mixture is stirred at 50°–55° C. for 3 hours, whereupon analysis reveals that all the mercaptophenol has been consumed and a minor amount of reactant is still present. Therefore, additional 2.43 grams of mercaptophenol is added and stirring continued for several hours. Two additional portions of the mercaptophenol (3.64 and 0.5 grams) with additional heating are then added in like manner, after which analysis indicates that the reaction is now essentially complete. The reaction mixture is then washed with 2N sodium hydroxide solution, followed by water washing to a pH of 6–7 and drying over anhydrous sodium sulfate. The product is isolated by filtering off the drying agent, removal of the solvent by distillation at reduced pressure and finally crystallizing the residue from n-heptane to yield white crystals melting at 125° to 126.5° C.

Anal. Calcd. for $C_{46}H_{70}O_3S_3$: C, 72.01; H, 9.2. Found: C, 71.08; H, 8.9.

EXAMPLE 4

1,1-Bis-(3,5-di-tert-butyl-4-hydroxyphenylthio)-3-(n-dodecylthio)butane (a) 3-(n-Dodecylthio)-n-butanal 14.02 Grams of crotonaldehyde (0.20 mole) is added dropwise over a 40-minute period at 60° to 65° C. to a solution of 41.2 grams of n-dodecyl mercaptan (0.20 moles) and 0.66 grams of triethylamine after which heating and stirring are continued at 85° C. for 1.5 hours. Analysis of the reaction mixture indicates that the reaction is then substantially complete. The product is isolated as a light yellow liquid by stripping off the volatiles.

(b) 2.72 Grams of the product of (a) and 95 mg of p-toluenesulfonic acid are added with stirring to a solution of 2,6-di-tert-butyl-4-mercaptophenol. The reaction mixture is then heated at 50°–55° C. for five hours. The toluene solution is successively washed with water, saturated sodium bicarbonate and water. It is then dried over anhydrous sodium sulfate. Filtration to remove the drying agent and the solvent removed by distillation at reduced pressure at 0.15 mm Hg. for 1 hour yields the product as a liquid. The product dissolved in a solvent mixture (60:40) of heptane and toluene is purified by flash chromatography after removal of volatiles at 75°–80° C. and 0.20 mm Hg. for four hours to yield the product as a light yellow liquid.

Anal. Calcd. for $C_{44}H_{74}O_2S_3$: C, 72.27; H, 10.20. Found: C, 72.47; H, 10.37.

EXAMPLE 5

4-Methyl-2,2,4-tris(3,5-di-tert-butyl-4-hydroxyphenyl-thio)pentane (a) 4-Methyl-4-(3,5-di-tert-butyl-4-hydroxyphenylthio)-2-pentanone 8.48 Grams of mesityl oxide (0.084 moles) is added dropwise to a solution of 21.0 grams of 2,6 di-tert-butyl-4-mercaptophenol (0.088 moles) and one gram of triethylamine in 30 ml of toluene. The mixture is heated in 50°–55° C. for six hours. The solvent is then stripped off under vacuum and the residue retained at 60°–65° C. and 0.20 mm. Hg. for two hours. The residue is dissolved in toluene and purified by flash chromatography using silica gel. The product is isolated from solution by distilling off the volatiles under vacuum to a final pressure of 0.10 mm. Hg for five hours.

Anal. Calcd. for $C_{20}H_{32}O_2S$: C, 71.37; H, 9.58. Found: C, 71.25; H, 9.41.

(b) 0.11 Grams of $BF_3$-etherate is added to a solution of 2.70 grams of the product from (a) and 4.14 grams of 2,6-di-tert- butyl-4-mercaptophenol dissolved in 30 ml of toluene. The mixture is heated at 55°–65° C. for nine hours and 105°–110° C. for three additional hours. The toluene solution is washed with water and dried over sodium sulfate. The residue, isolated by evaporation of the solvent by distillation in vacuum, is purified by passing a solution in 70:30 heptane:toluene through a flash chromatographic column using silica gel. The isolated residue solidifies on cooling, and melts at 93°–115° C.

Anal. Calcd. for $C_{48}H_{74}O_3S_3$: C, 72.48; H, 9.38. Found: C, 72.49; H, 9.40.

EXAMPLE 6

1,1,3-Tris-(3-tert-butyl-4-hydroxy-5-methylphenylthio)butane (a) 3-(3-Tert-butyl-4-hydroxy-5-methylphenylthio)-butanal Reaction of a one molar proportion of n-butanal with a one molar proportion of 2-tert-butyl-6-methyl-4-mercaptophenol in the presence of triethylamine by substantially the method described in Example 3(a) yields the product which is substantially the desired substituted n-butanal analogous to the product of Example 3(a).

(b) The instant compound named above is made in an analogous manner to the compound of Example 3 by reacting a one molar proportion of reactant (a) with two molar proportions of 2-tert-butyl-6-methyl-4-mercapto-phenol. After recrystallization from a solvent mixture of 12:1 heptane: toluene, the compound is isolated as white crystals melting at 65°–69° C.

Anal. Calcd. for $C_{37}H_{52}O_3S_3$: C, 69.32; H, 8.17; S, 15.0. Found: C, 71.25; H, 9.41; S, 14.6.

EXAMPLE 7

1,1,3,5-Tetrakis(3,5-di-tert-butyl-4-hydroxyphenylthio)-hexane (a) Reaction product of a 2:1 molar ratio of 2,6-di-tert-butyl-4-mercaptophenol and 2,4-hexadienal 12.2 Grams (0.05 moles) of 2,6-di-tert-butyl-4-mercaptophenol, 2.4 grams of 2,4-hexadienal and 0.5 grams of triethylamine are dissolved together in 50 ml of toluene at 20° C. to yield a clear solution. This solution is heated at 55°–65° C. for 37 hours. The product is isolated by stripping off the volatiles under vacuum at 0.2 mm Hg. for one hour. Analysis indicates that the product is primarily 3,5-bis(3,5-di-tert-butyl-4-hydroxyphenylthio)-hexanal.

(b) 0.17 Grams of $BF_3$-etherate is added to a solution of 14.5 grams of the product of (a) and 12.2 grams of 2,6-di-tert-butyl-4-mercaptophenol under stirring at room temperature and then at 50°–55° C. The reaction mixture is diluted with 50 ml of toluene, washed successively with water, twice with 2N sodium hydroxide solution, and again with water, and dried over anhydrous sodium sulfate. The drying agents and volatiles are removed, whereupon the isolated residue is dissolved in a hot solvent mixture of 70 ml of n-heptane and 20 ml of isopropanol and allowed to crystallize to yield white crystals melting at 160°–162° C.

Anal. Calcd. for $C_{62}H_{94}O_4S_4$: C, 72.18; H, 9.18. Found: C, 72.3; H, 9.3.

EXAMPLE 8

1,1,3-Tris(3-methyl-5-tert-butyl-4-hydroxyphenylthio)-cyclohexane

When, using the general procedure of Example 6, an equivalent amount of 2-cyclohexen-1-one is substituted for crotonaldehyde, the above-named compound is prepared.

EXAMPLE 9

1,1,3-Tris(3,5-di-tert-amyl-4-hydroxyphenylthio)propane

When, using the general procedure of Example 3, equivalent amounts of acrolein and 2,6-di-tert-amyl-4-mercaptophenol are substituted respectively for crotonaldehyde and 2,6-di-tert-butyl-4-mercaptophenol, the above-named compound is obtained.

EXAMPLE 10

1,1,3-Tris(3-tert-butyl-5-tert-octyl-4-hydroxyphenylthio)-3,5,5-trimethylcyclohexane When, using the general procedure of Example 5, equivalent amounts of isophorone and 2-tert-butyl-6-tert-octyl-4-mercaptophenol are substituted respectively for mesityl oxide and 2,6-di-tert-butyl-4-mercaptophenol, the above-named compound is obtained.

EXAMPLE 11

1,1,3-Tris(3,5-di-tert-butyl-4-hydroxyphenylthio)-3-phenylpropane

When, using the general procedure of Example 3, an equivalent amount of cinnamaldelyde is substituted for crotonaldehyde, the above-named compound is prepared.

EXAMPLE 12

This example illustrates the stabilizing effectiveness of the instant stabilizers in impact polystyrene (IPS).

In the laboratory procedure utilized herein, a solution of eight weight percent polybutadiene rubber (Firestone -DIENE 55) dissolved in styrene monomer is prepared on a roller mill. The indicated amount of stabilizer is also introduced at this point. 500 ppm of zinc stearate is added to aid in removing the sample from the bottle after the polymerization. The bottle is screwed into the polymerization apparatus which is equipped with a double helical ribbon stirrer. Since most commercial IPS bulk polymerizations are thermally initiated processes, no initiator is used in the laboratory process. A nitrogen atmosphere is established and the reactor is then heated to 121° C. within ½ hour. Heating continue at 121° C. with efficient stirring until there is a 30 to 35% monomer conversion (ca. 2.5 hours). The stirring rate is controlled to yield a two to four micron rubber particle size. The bottles are removed from the polymerization apparatus, blanketed with nitrogen, capped, and then placed in a fluidized bed sand bath to complete the polymerization. The bottles are heated in the bath in the following fashion: one hour at 100° C. to equilibrate the temperature, one hour to reach 140° C. and then an additional eight hours with the temperature increasing at the rate of 10° C. per hour to a maximum of 220° C. After the resin is cooled, the bottle is broken and the glass is removed. The average weight of the polymer block is slightly over 600 grams. The block is then placed into a vacuum oven at 200° C. and a vacuum of 1 mm applied as the polymer is heated for 45 minutes in order to remove all volatiles. The block is removed from the oven, immediately placed in a heated (205° C.) hydraulic press and then pressed into a thick slab between two sheets of aluminum foil (three minutes heating, five minutes in a cold press). The slab is split with a band saw and the pieces are granulated.

All batches were extruded at 205° C. and then pelletized. The pellets are compression molded at 205° C. into 125 mil (3.175 mm) tensile bars. The bars are then aged at 150° C. on glass plates placed on rotating shelves in a forced air oven. Other tensile bars are aged at 80° C. suspended from rotating shelves in a forced air oven. The specimen yellowness index is determined on the bars at various intervals according to ASTM D-1925-63T.

| | | Oven Aged Samples at 80° C. | | | | |
|---|---|---|---|---|---|---|
| | Conc. (% by | % Elongation (Hours at 80° C.) | | | | |
| Additive | wt.) | 0 | 300 | 600 | 900 | 1200 |
| None | — | 33 | 9 | 3 | 3 | 3 |
| Compound of Example 1 | 0.1 | 42 | 36 | 23 | 12 | 10 |
| | | Yellowness Index | | | | |
| None | — | 7 | 14 | 45 | 59 | — |
| Compound of Example 1 | 0.1 | 11 | 22 | 36 | 43 | 45 |

| | | Oven Aged Samples at 150° C. | | | | |
|---|---|---|---|---|---|---|
| | Conc. (% by | % Elongation (Hours at 150° C.) | | | | |
| Additive | wt.) | 0 | ½ | 1 | 1½ | 2 |
| None | — | 33 | 7 | 7 | 3 | 3 |
| Compound of Example 1 | | 42 | 36 | 30 | 22 | 10 |
| None | — | 25 | 13 | 4 | 3 | 3 |
| Compound of Example 3b | | 65 | 60 | 52 | 42 | 33 |
| Compound of Example 4b | 0.1 | 72 | 47 | 29 | 18 | 7 |
| | | Yellowness Index | | | | |
| None | — | 7 | 18 | 30 | 38 | 43 |
| Compound of Example 1 | 0.1 | 11 | 10 | 27 | 31 | 33 |
| None | — | −1.3 | −0.6 | 3.7 | 61 | 10.9 |
| Compound of Example 3b | 0.1 | 0 | 6 | 10 | 12 | 14 |
| Compound of Example 4b | 0.1 | −.3 | 6 | 9 | 8 | 14 |

EXAMPLE 13

Unstabilized polypropylene powder (Hercules Profax 6501) is thoroughly blended with 0.2%, by weight, of additive. The blended materials are then milled on a two roll mill at 182° C. for 5 minutes, after which time the stabilized polypropylene is sheeted from the mill and allowed to cool.

The milled polypropylene is then cut into pieces and compression molded on a hydraulic press at 220° C. at 175 psi (12.3 Kg/cm$^2$) into 5 mil (0.127 mm) films. The samples are exposed to a fluorescent sunlight/black light chamber until failure. Failure is determined as the time required to reach 0.5 carbonyl units in the infrared spectrum a value associated with degradation of film properties.

| Additive | Hours to Failure |
|---|---|
| None | 200–300 |
| Compound of Example 1 | 530 |
| Compound of Example 2 | 450 |
| Compound of Example 3b | 480 |
| Compound of Example 4b | 470 |

EXAMPLE 14

The oxidation stability of milled polypropylene containing, respectively, 0.2%, by weight, of the instant additives as well as of a synergized formulation containing 0.1%, by weight, of the additive in the presence of 0.3%, by weight, distearyl thiodipropionate (DSTDP) on plaques of 25 mil (0.635 mm) thickness is determined by exposing said plaques to air in a forced draft oven at 150° C. The plaques are considered to have failed on showing the first signs of decomposition (e.g. cracking or brown edges).

| | Time to Failure (Hrs) | |
|---|---|---|
| Additive Compound of | Additive Conc. 0.2% by wt | Synergized Composition (% by wt) 0.1% Additive + 0.3% DSTDP |
| Base Resin (no DSTDP) | 3 | — |
| (with 0.3% DSTDP) | — | 60–90 |
| Example 1 | 120 | 250 |

-continued

| Additive Compound of | Time to Failure (Hrs) | |
|---|---|---|
| | Additive Conc. 0.2% by wt | Synergized Composition (% by wt) 0.1% Additive + 0.3% DSTDP |
| Example 2 | 220 | 370 |
| Example 3b | 260 | 490 |
| Example 4b | 360 | 540 |

EXAMPLE 15

Mineral Oil Oxidation Test (a) Rotary Bomb Oxidation Test

This test is carried out under the directions of ASTM D-2272. To the glass container fitted with a copper coil is added 50 grams of oil and 5 ml of water. The sample container is then inserted into the test bomb containing another 5 ml of water. The bomb is then sealed with a cap fitted with a pressure gage and stirrer. The bomb is then flushed with oxygen. The oxygen supply is then adjusted to a pressure of 90 psi (6.3 kg/cm$^2$) with the oxygen supply tank held at 77° F. (25° C.). For each 5.1° F. (2.8° C.) above or below this temperature one pound of oxygen is added or subtracted to attain the initial pressure. The bomb is then filled to said pressure (90 psi, 6.3 kg/cm$^2$) with oxygen, and inlet valve then closed.

The bomb is placed in the bath at 150° C. with the stirrer set to rotate at 100±5 rpm. The test is complete when the pressure drops more than 25 psi (1.75 kg/cm$^2$) below the maximum pressure. The time in minutes from the start of the test to the 25 psi (1.75 kg/cm$^2$) pressure drop is the measure of the oxidation stability of the oil.

| Rotary Bomb Oxidation Test | |
|---|---|
| Additive of (0.25% by wt) | Time to Failure (Minutes) |
| Oil only (Exxon 1243) | 31 |
| Example 3b | 166 |
| Example 4b | 201 |
| Example 7 | 177 |

(b) Turbine Oil Oxidation Test

This test method is intended for the determination of oxidation life of inhibited turbine oils by the directions of ASTM D-943.

The apparatus consists of a constant-temperature bath thermostatically controlled to maintain the immersed oil sample cell at a temperature of 95±0.2 C.

The oxidation cell or glass tube containing the oil sample is 45 mm in diameter and 600 mm in length. The catalyst consists of open-hearth steel wire and electrolytic copper wire (both #14 gage, 0.064 inch, 1.63 mm in diameter) prepared in coil form. The oxygen flowmeter regulates the flow from an oxygen cylinder, bubbling through the oil at 3 liters per hour, with an accuracy of ±0.1 liter per hour. The apparatus is assembled with catalyst coils over the inlet of the oxygen delivery tube, and the assembly is placed in the test tube centering both coils and oxygen tube. The 300-ml oil sample covers the catalyst coils wetting them completely. The entire cell is immersed in the warm heating bath so that the liquid is at least 75 mm above the oil sample. The mushroom condenser is placed over the oxygen delivery tube and test tube, and connections are made to the cooling water. Distilled water (60 ml) is added to the oxidation cell and supplemented as required to maintain the water level between the oxygen outlet and the shoulder of the oxygen delivery tube.

The acid number as determined by ASTM D-974 test for neutralization value is the determining factor in the test.

Failure is taken as the time to reach an acid value of 2.0.

| Turbine Oil Oxidation Test | |
|---|---|
| Additive of (0.25% by wt) | Time to Failure Hours |
| Oil only (Exxon LO5084) | 130 |
| Example 4b | 1800 |

These examples thus indicate the excellent stabilizing performance of the instant compounds in several substrates.

Summarizing, it is seen that this invention provides a group of compounds having excellent stabilizing activity in a variety of organic materials. Variations may be made in proportions, procedures and materials without departing from the scope of the invention as defined by the following claims.

What is claimed is:

1. A compound of formula I $$(T-S)_n-\underset{\underset{(T_5)_t}{|}}{\overset{\overset{T_4}{|}}{C}}-E-\underset{\underset{T_3}{|}}{C}\!\!+\!\!S-\!\!\left\langle\!\!\bigcirc\!\!\right\rangle\!\!-OH)_2 \qquad (I)$$

with $T_1$ and $T_2$ on the ring wherein $T_1$ and $T_2$ are independently alkyl of 1 to 12 carbon atoms, cycloalkyl of 5 to 6 carbon atoms, phenyl, phenyl substituted by alkyl of 1 to 12 carbon atoms, phenylalkyl of 7 to 9 carbon atoms or said phenylalkyl substituted by alkyl of 1 to 12 carbon atoms, $T_2$ may also be hydrogen, T is alkyl of 1 to 24 carbon atoms, phenyl, phenyl substituted by alkyl of 1 to 12 carbon atoms, or the group $$HO-\!\!\left\langle\!\!\bigcirc\!\!\right\rangle\!\!-,$$

with $T_1$ and $T_2$ on the ring

E is a direct bond, alkylene of 1 to 11 carbon atoms, cycloalkylene of 5 to 6 carbon atoms or phenylene, or is the group $$-CH_2CHCH_2-,\\ \underset{ST}{|}$$

$T_3$ and $T_4$ are independently hydrogen, alkyl of 1 to 30 carbon atoms, said alkyl substituted by phenyl or by phenyl substituted by alkyl of 1 to 12 carbon atoms, cycloalkyl of 5 to 6 carbon atoms, or T₃ and T₄ together are straight- or branched-chain alkylene of 3 to 7 carbon atoms when E is methylene, T₅ is hydrogen, alkyl of 1 to 4 carbon atoms or phenyl, n is 1 or 2, t is 0 or 1, and t is 2-n.

2. A compound according to claim 1 where T₂ is in the ortho position to the hydroxy group.

3. A compound according to claim 2 wherein T₁ and T₂ are independently alkyl of 1 to 8 carbon atoms.

4. A compound according to claim 3 wherein T₁ is methyl or tert-butyl and T₂ is tert-butyl.

5. A compound according to claim 4 wherein T₁ is tert-butyl.

6. A compound according to claim 1 wherein T is alkyl of 7 to 18 carbon atoms or is the group

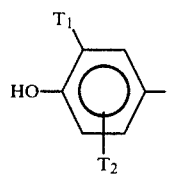

where T₁ and T₂ are defined in claim 1.

7. A compound according to claim 1 wherein E is a direct bond, alkylene of 1 to 6 carbon atoms or the group

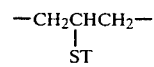

where T is defined in claim 1.

8. A compound according to claim 1 wherein T₃ and T₄ are independently hydrogen or alkyl of 1 to 4 carbon atoms; or T₃ and T₄ together are trimethylene or 2,2-dimethylpropan-1,3-diyl when E is methylene.

9. A compound according to claim 1 wherein T₅ is hydrogen or methyl.

10. A compound according to claim 1 which is 1,1,2,2-tetrakis(3,5-di-tert-butyl-4-hydroxyphenylthio)ethane.

11. A compound according to claim 1 which is 1,1,5,5-tetrakis(3,5-di-tert-butyl-4-hydroxyphenylthio)pentane.

12. A compound according to claim 1 which is 1,1,3-tris(3,5-di-tert-butyl-4-hydroxyphenylthio)butane.

13. A compound according to claim 1 which is 1,1-bis(3,5-di-tert-butyl-4-hydroxyphenylthio)-3-(n-dodecylthio)butane.

14. A compound according to claim 1 which is 1,1,3-tris(3-tert-butyl-5-tert-octyl-4-hydroxyphenylthio)-3,5,5-trimethylcyclohexane.

* * * * *